(12) United States Patent
Hartmann et al.

(10) Patent No.: US 9,555,172 B2
(45) Date of Patent: Jan. 31, 2017

(54) METHOD FOR DETERMINING STRATEGIC EXPRESSION REGIME FOR USING A BREASTPUMP

(75) Inventors: Peter Hartmann, Gooseberry Hill (AU); Ching Tat Lai, Canning Vale (AU); Leon R. Mitoulas, Cham (CH)

(73) Assignee: Medela Hodling AG, Baar (CH)

( * ) Notice: Subject to any disclaimer, the term of this patent is extended or adjusted under 35 U.S.C. 154(b) by 1068 days.

(21) Appl. No.: 11/903,363

(22) Filed: Sep. 21, 2007

(65) Prior Publication Data

US 2008/0097376 A1 Apr. 24, 2008

Related U.S. Application Data

(60) Provisional application No. 60/846,646, filed on Sep. 22, 2006.

(51) Int. Cl.
*A61M 1/06* (2006.01)
*A61J 13/00* (2006.01)

(52) U.S. Cl.
CPC ............. *A61M 1/06* (2013.01); *A61J 13/00* (2013.01); *A61M 2205/52* (2013.01)

(58) Field of Classification Search
CPC ....... A61M 1/06; A61M 2205/52; A61J 13/00
USPC ............................................. 604/74–76, 500
See application file for complete search history.

(56) References Cited

FOREIGN PATENT DOCUMENTS

EP 1430918 A1 6/2004
WO WO 2004/026368 4/2004

OTHER PUBLICATIONS

Daly, Steven E. J., Kent, Jacqueline C., Owens, Robyn A., and Hartmann, Peter E. "Frequency and degree of milk removal and the short-term control of human milk synthesis". Experimental Physiology (1996). vol. 81, pp. 861-875.*
Mitoulas, L.R. et al. "Efficacy of Breast Milk Expression Using an Electric Breast Pump". Journal of Human Lactation, vol. 1, No. 4, pp. 344 to 352, 2002. See whole document.
Mitoulas, L.R. et al., "Effect of Vacuum Profile on Breast Milk Expression Using an Electric Breast Pump" Journal of Human Lactation, vol. 18. pp. 353-360, 2002. See whole document.
ABM Protocols, "Protocol #10: Breastfeeding the near term infant (35 to 37 weeks gestation)". The Academy of Breastfeeding Medicine, Mar. 14, 2006 [ retrieved from Dec. 12, 2007], Retrieved from <URL:http://www.bfmed.org/ace-files/protocol/near_term.pdf> Whole document.
Kent, J.C. et al., "Response of Breasts to Different Stimulation Patterns of an Electric Breast Pump" Journal of Human Lactation, vol. 19, No. 2, pp. 179 to 186, 2003. See whole document.
ABA Booklet: "Suggestions on using an Electric Breast Pump", Revised Jan. 2006 [ retrieved Dec. 12, 2007], Retrieved from <URL: http://www.breastfeeding.asn.au/binfo/pumpsug.html>.

(Continued)

*Primary Examiner* — Bhisma Mehta
*Assistant Examiner* — Larry R Wilson
(74) *Attorney, Agent, or Firm* — McDonnell Boehnen Hulbert & Berghoff LLP

(57) ABSTRACT

The present invention is directed to a method of determining a strategic expression regime for a pump-dependent mother that optimizes the mother's milk production while minimizing the demands on the mother. The regime takes into account the impact of the interval between breast expressions on milk yield for individual breasts within the mother.

16 Claims, 17 Drawing Sheets

(56) References Cited

OTHER PUBLICATIONS

Kent, J.C. et al., "Volume and Frequency of Breastfeedings and Content of Breast Milk Throught the Day". Pediatrics, vol. 117 (3), pp. e387 to e395, Mar. 2006. See p. e388, Paragraph 2 & p. e393, last paragraph.

Janet, "A Different Kind of Breastfeeding Mother" from New Beginnings, vol. 19, No. 1, Jan.-Feb. 2002, p. 9 [ retrieved on Dec. 12, 2007], Retrieved from < URL: http://www.illi.org/NB/NBJanFeb02p9a.html> Whole document.

Daly Steven et al, "Infant Demand and milk supply. Part 2: the short term control of milk synthesis in lactating women", Journal of Human Lactation, vol. 11(1), pp. 27-37, Mar. 1, 1995. See p. 32, col. 2, lines 1-3.

Department of Labour Booklet, "Breastfeeding in the Workplace— An Employer's Guide to Making it Work", Jun. 2005, [retrieved Dec. 12, 2007], Retrieved from <URL: http://www.ers.dol.govt.nz> Whole document.

ABM Protocols, "Protocol #7: Model Breastfeeding Policy". The Academy of Breastfeeding Medicine, Apr. 26 2006.[ retrieved on Dec. 12, 2007], Retrieved from <URL: http"//www.bfmed.org/ace-files/protocol/mphpolicy_ABM.pdf> Whole Document.

PCT International Search Report for PCT/AU2007/001413.

Daly, Steven E.J., et al., "Frequency and Degree of Milk Removal and the Short-Term Control of Human Milk Synthesis," Experimental Physiology (1996), 81, 861-875.

European Search Report for European Application EP 07 81 5231 mailed Mar. 20, 2014.

Kent J.C. et al., "Response of Breasts to Different Stimulation Patterns of an Electric Breast Pump," Journal of Human Lactation, vol. 19, No. 2., Jan. 1, 2003, pp. 179-186.

Hartmann P.E., "Infant Demand and Milk Supply. Part 2: The Short Term Control of Milk Synthesis in Lactating Women," Journal of Human Lactation, vol. 11, No. 1, Mar. 1, 1995, pp. 27-37.

Protocol #10: Breastfeeding the near term infant (35 to 37 weeks gestation), ABM Protocols, Academy of Breastfeeding Medicine, Mar. 14, 2006.

ABA Booklet: Suggestions on Using an Electric Breast Pump, Internet Citation, Jan. 27, 2006, pp. 1-3.

* cited by examiner

METHOD FOR DETERMINING STRATEGIC EXPRESSION REGIME FOR USING A BREASTPUMP

APPLICATION HISTORY

Applicant claims the benefit of prior U.S. Provisional Application Ser. No. 60/846,646, filed on Sep. 22, 2006, entitled "Expression Regimes of Preterm Mothers."

BACKGROUND

1. Field of the Application

The invention relates generally to the expression of breast milk. More particularly, the present invention relates to a method of determining a strategic expression regime for mothers who are using a breastpump.

2. Description of the Related Art

Almost all mothers who deliver at term have the physiological capacity to provide milk for their babies. Once lactation is established, the appetite of the baby regulates milk production by local inhibition of milk synthesis independently in each breast as milk accumulates between breastfeedings.

Many mothers who deliver prematurely have a delayed initiation of lactation and are more likely to have a low milk supply. Furthermore, the inability of preterm babies to feed directly from the breasts (for example, due to either sickness or the immature co-ordination of the suck, swallow and breathe reflex) results in their mothers having to use some other means for milk expression, and thereby still provide breast milk for their babies. Thus, these mothers most often use a breastpump for both the initiation and maintenance of their milk supply.

Current expression recommendations particularly for pre-term mothers show that increased milk-expression frequency results in an increase in daily milk production. Furthermore, the mechanism controlling the response to expression frequency appears to act locally, at the level of each mammary gland, rather than through a more systemic response. DeCarvalho et al. (1985) was the first to report a strong correlation between daily milk production and frequency of expression, and encouraged preterm mothers to have a frequent milk expression regime that enhanced the likelihood of lactation success. This frequent milk expression regime is now widely practiced. According to this regime, preterm mothers should express frequently (e.g., 6 times per day), and at least 100 minutes per day. In addition, recent studies showed high frequency of breastmilk expression could improve the success of the initiation of lactation, especially for preterm mothers (Hill et al. 2001).

Therefore, there is a general perception that increased expression frequency will result in an increased daily milk production. Obviously, this is a very demanding recommendation for mothers, particularly those who are very concerned about their often fragile, preterm babies. Interestingly, the studies on which these recommendations are based are on milk production per mother, rather than per breast. Consequently, the recommendations do not take into account potential differences between breasts of an individual.

The concept of the autocrine inhibition of milk production, as a result of the accumulation of an inhibitory factor in the milk of a full breast, seems to conveniently explain the observation of increased milk production associated with more frequent breastfeeding and/or breast expression. Furthermore, it has been suggested that the factor acted by a unique mechanism that inhibited the secretion of milk from the Golgi vesicles (Rennison et al. 1993). This enabled a rapid downward regulation of secretion, as milk accumulated in the breast with longer intervals between milk removal. However, Daly et al. (1996) found that the inhibition of milk synthesis in the breast of mothers who delivered at term occurred after intervals of more than six to eight hours. As this study found with term mothers, the large variation of milk yield from each breast resulted in difficulties in assessing the impact of the expression regime on the milk production. Expressing the volume per expression as a proportion of 24 hour milk production (actual milk yield) standardized the difference in the milk yield between breasts, and allowed the analysis of a relationship between proportional milk yield and interval since previous expression. Furthermore, by expressing the 24 hour milk production as 100%, the cumulative expected milk yield (expected milk yield) curve could be calculated essentially for all times from 0 to 24 hours, assuming that the rate of milk synthesis over the day was constant.

Clinically, the goal for pre-term mothers for their total daily milk production has been set in the range of about 350 g/24 hr (Meier et al., personal communication) and 500 ml/24 hr (Hill et al. 2005). There are, however, no consistent guidelines for the volume of milk that these mothers either can or should produce per day. For instance, the minimum daily milk production that mothers should aim for is the minimum volume of milk required for an exclusively breast-fed babies at 1-6 months, which is considered to be about 440 ml/24 hr (Kent et al., 2006).

Current expression regimes can place a great demand on mothers who for many reasons do not have the ability to basically be "on-call" to breastfeed a baby; this is especially true for preterm mothers, who are already in a time of extreme stress. Hence, a method that can optimize milk production and minimize the effort for the mothers would greatly enhance their chance of having successful lactation. Further, although the short-term control of milk synthesis occurs at the level of the individual breasts, as a practical matter, expression regimes for mothers need to be similar for both their breasts.

SUMMARY OF THE INVENTION

The present invention variously meets these foregoing objectives, and more, by providing a method of determining milk production capacity of a nursing mother, comprising the steps of measuring the volume of milk produced in at least three pumping sessions. The first pumping session is the first milk expression for a day, which is intended to be the initial pumping session having a very significantly higher milk output than following sessions. The second pumping session occurs after the first pumping session, and a following pumping session occurs after the second session, which could be a third or subsequent session. The method uses the milk volume measured in the following session as an average yield of milk production per pumping session.

In one embodiment, the present invention provides a method of determining a strategic expression regime for mothers who are using breastpumps. The method requires expressing milk from the mother at certain intervals during a day, and then measuring the amount of milk expressed at each interval to determine milk volume. A regression analysis is performed to predict the amount that the interval of expression can be extended without compromising milk production. Based upon the regression analysis, an expression protocol for the mother is provided, balancing and indeed optimizing frequency of expression with volume of production.

In another embodiment, the present invention provides an improved method for expressing milk by a nursing mother using a breastpump without significantly compromising milk production. The improvement comprises expressing milk in intervals separated by about five to about seven hours.

These as well as other aspects and advantages of the invention will become further apparent to those of skill in the art by reading the following detailed description, with reference where appropriate to the accompanying drawings. Further, it should be understood that the embodiments described herein are intended to illustrate the invention by way of example only.

BRIEF DESCRIPTION OF THE DRAWINGS

Exemplary embodiments of the invention are described herein with reference to the drawings, in which.

DETAILED DESCRIPTION OF EMBODIMENTS OF THE INVENTION

The method of determining a strategic expression regime for a pump-dependent mother of the present invention had its genesis from two studies, the details of which are discussed below.

A study was conducted with the aim to minimize the influence of the autocrine inhibition of milk production in mothers by the frequent expression of their breasts (breasts expressed each hour), and then to observe the effect of this increased frequency of breast expression for periods of up to seven hours.

Figure 1:
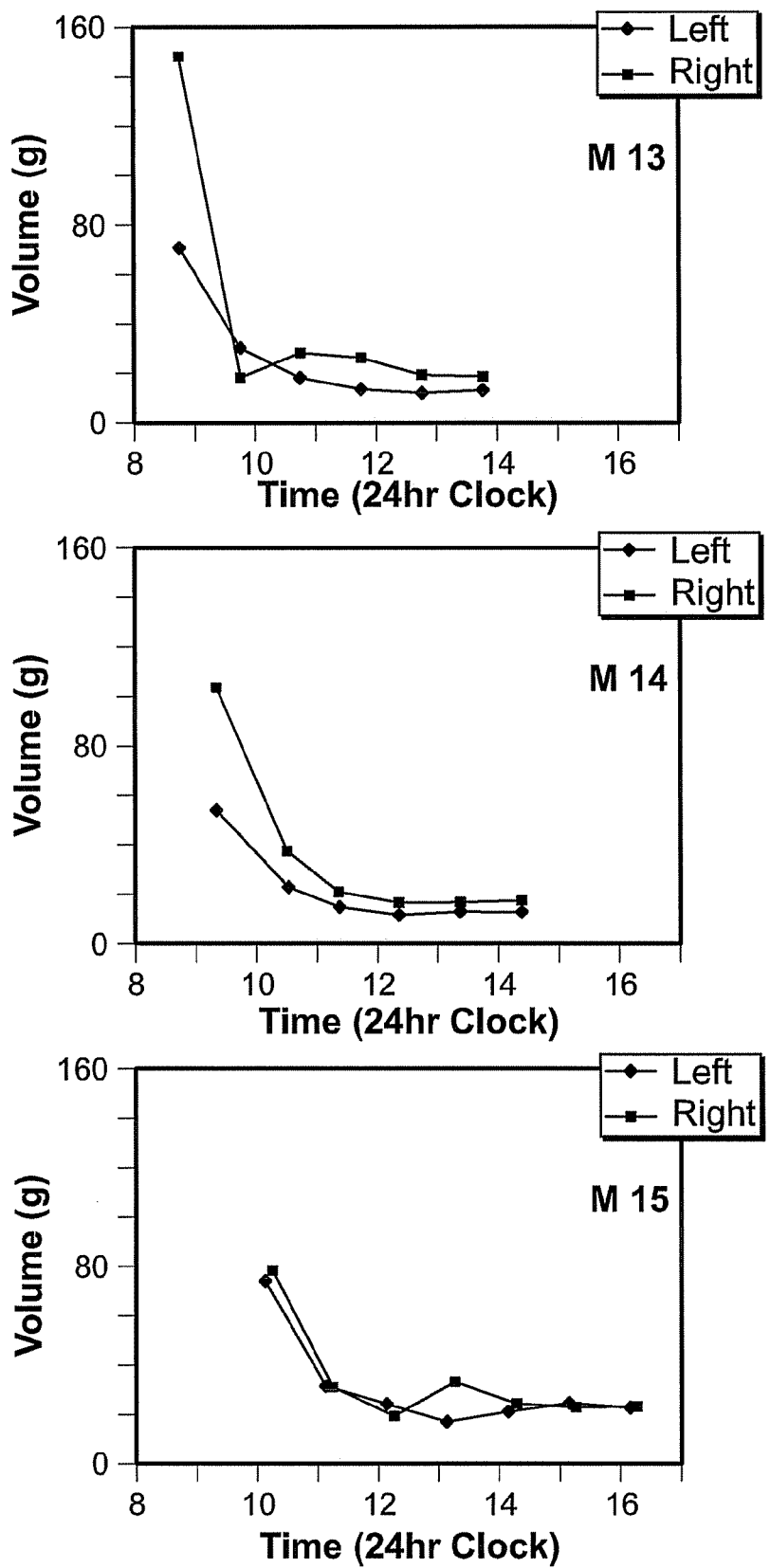
FIG. 1 shows milk volume at each pumping in an exemplary hourly pumping session.

Typical patterns for the hourly pumping sessions for these women are shown in FIG. 1. Higher volumes of milk were pumped at the first expression, followed by a decline in volume in the next expressions, and then a plateau was observed for subsequent expressions.

Repeated measurements showed that the hourly rate of milk production from the 24-hour milk production was significantly less than the hourly rate recorded between zero and one hour. However, there were no significant differences ($p>0.05$) between the hourly rates of milk production from the 24-hour milk production for each breast and the hourly rates recorded between 1 and 2, 2 and 3, 3 and 4, 4 and 5, and 5 and 6, hours (FIG. 3).

The volume of milk obtained at the first expression of an hourly pumping session was always the highest, then the volume declined at the second expression and reached stable levels at the third and subsequent hourly expressions (FIG. 1). The higher volume of milk obtained in the first expression was expected, since the time of the mother's previous either breastfeed or breast expression was not prescribed, but was more than one hour before the start of the session. This observation was consistent with previous studies that have shown that on average during either a breastfeed or breast expression, about 67% of the available milk was removed (Kent et al. 2006). Somewhat unexpectedly, the volume of milk expressed at the second expression was significantly higher than the subsequent expressions; it is possible that an additional proportion of the "residual" milk was removed at this expression. But there was no significant difference in the volume of milk expressed between the third and subsequent expressions (FIG. 3). This suggested that the "residual" milk remained constant after the second expression and that the volumes of milk removed represented the volume of milk synthesized in the previous interval from the third to seventh hourly expressions.

Figure 2:
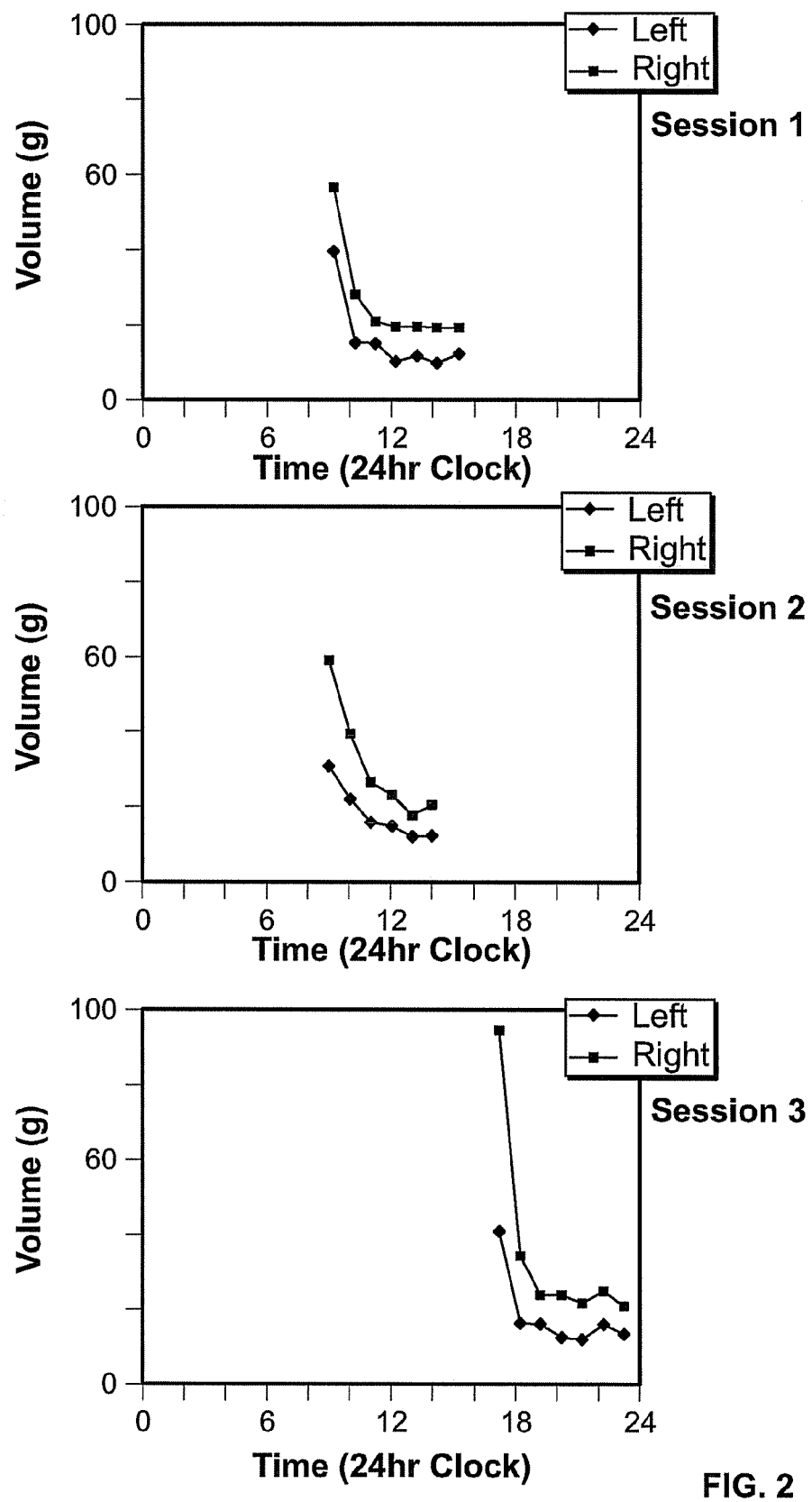
FIG. 2 shows milk volume for each pumping of an illustrative mother at three different hourly pumping sessions.
Figure 3:
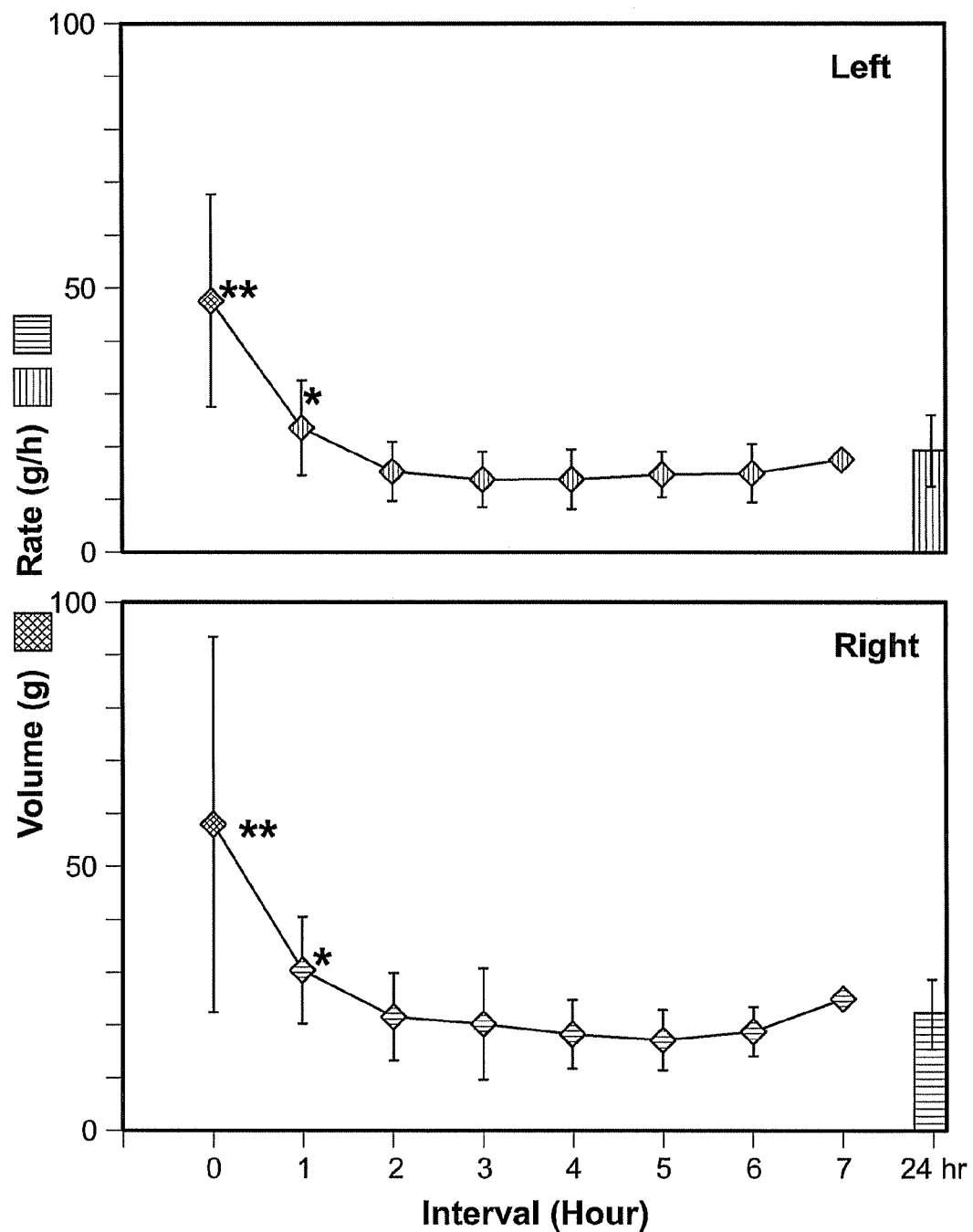
FIG. 3 shows an illustrative average hourly rate of milk production from hourly pumping and from 24 hour production.

It was then found that the relatively constant rates of milk production from the third to seventh expressions could occur at any time of day, as well as at different stages of lactation (FIG. 2), and the hourly rates of milk production from the third to seventh pumping were not significantly different from the average hourly rate of milk production calculated from the 24-hour measurement of milk production (FIG. 3). Furthermore, the hourly rates of milk production from the third to seventh pumping, obtained on different days for the same mother, were not significantly different (FIG. 2); the values obtained for the mother from two morning sessions were not significantly different to those obtained at an evening session (FIG. 2).

From this was concluded that the underlying rate of milk production from the third to seventh pumping represented the intrinsic synthetic (production) capacity of the breast. Therefore, the third expression, and following expressions, provide an estimate of the average hourly milk production for the 24-hour period. This procedure provides a very useful method of measuring daily milk production in women, as it is much easier than test weighing each breastfeed over a 24-hour period.

Another study was to observe milk production from days 15 to 20 postpartum in preterm mothers who were self-selecting their expression regimes, and to examine the impact of these expression regimes on milk production.

These women were recruited prior to the tenth day after giving birth, and recorded their milk production from each breast at each expression. The records included the starting and finishing times of each expression from each breast and the volume of milk (by weighing the bottle before and after an expression) of each expression from each breast.

The volume of milk from one expression divided by the time since the previous expression is termed the hourly rate. For each mother, coefficients of variation (CVs) were calculated for milk volume, interval between expressions and hourly rate. The relationship between the proportion (%) of daily milk yield and interval since previous expression was plotted against the expected percentage of daily milk production for hourly intervals of up to 14 hours.

Figure 4:
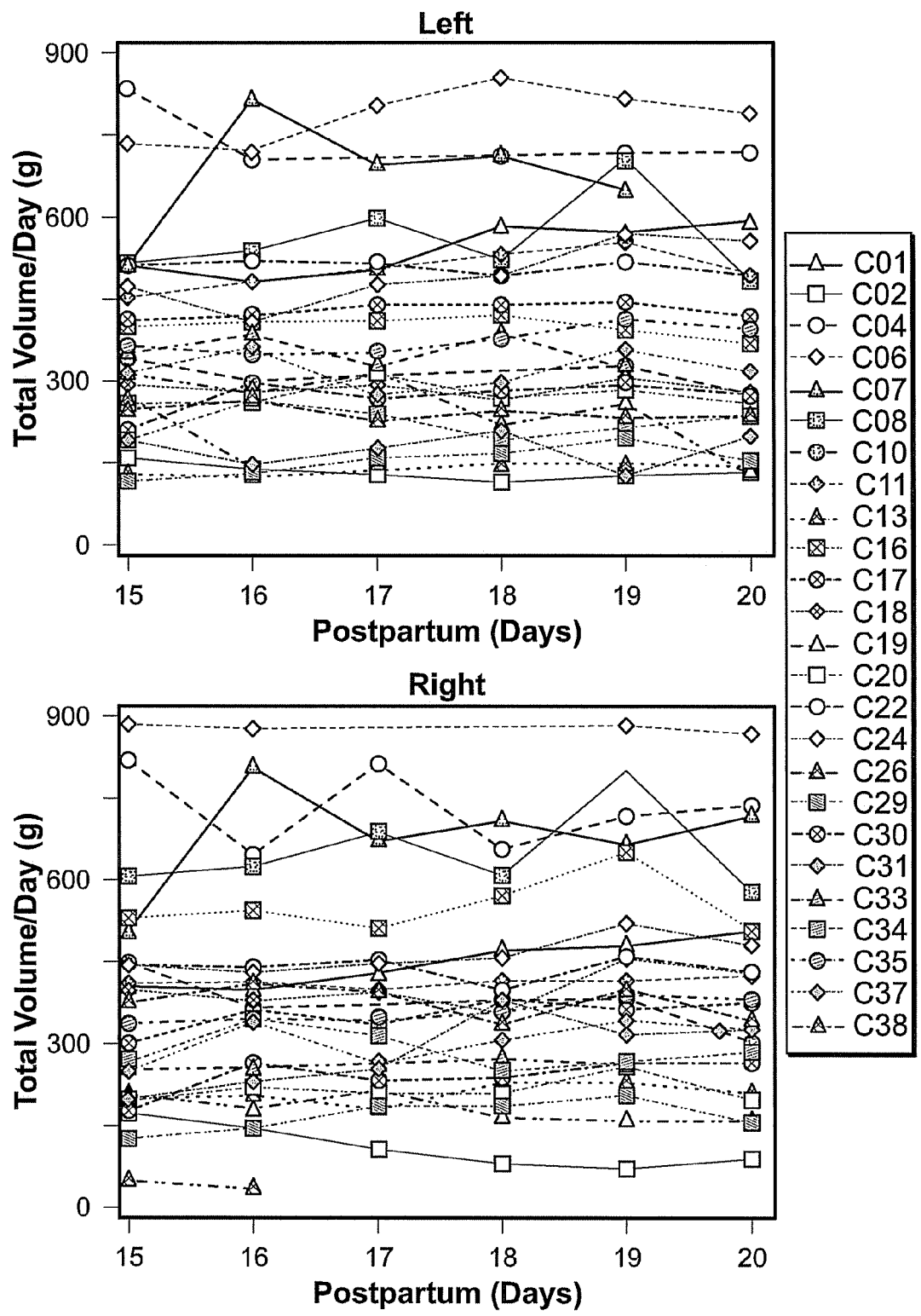
FIG. 4 shows total milk volume per day per breast for days 15 to 20 postpartum.
Figure 5:
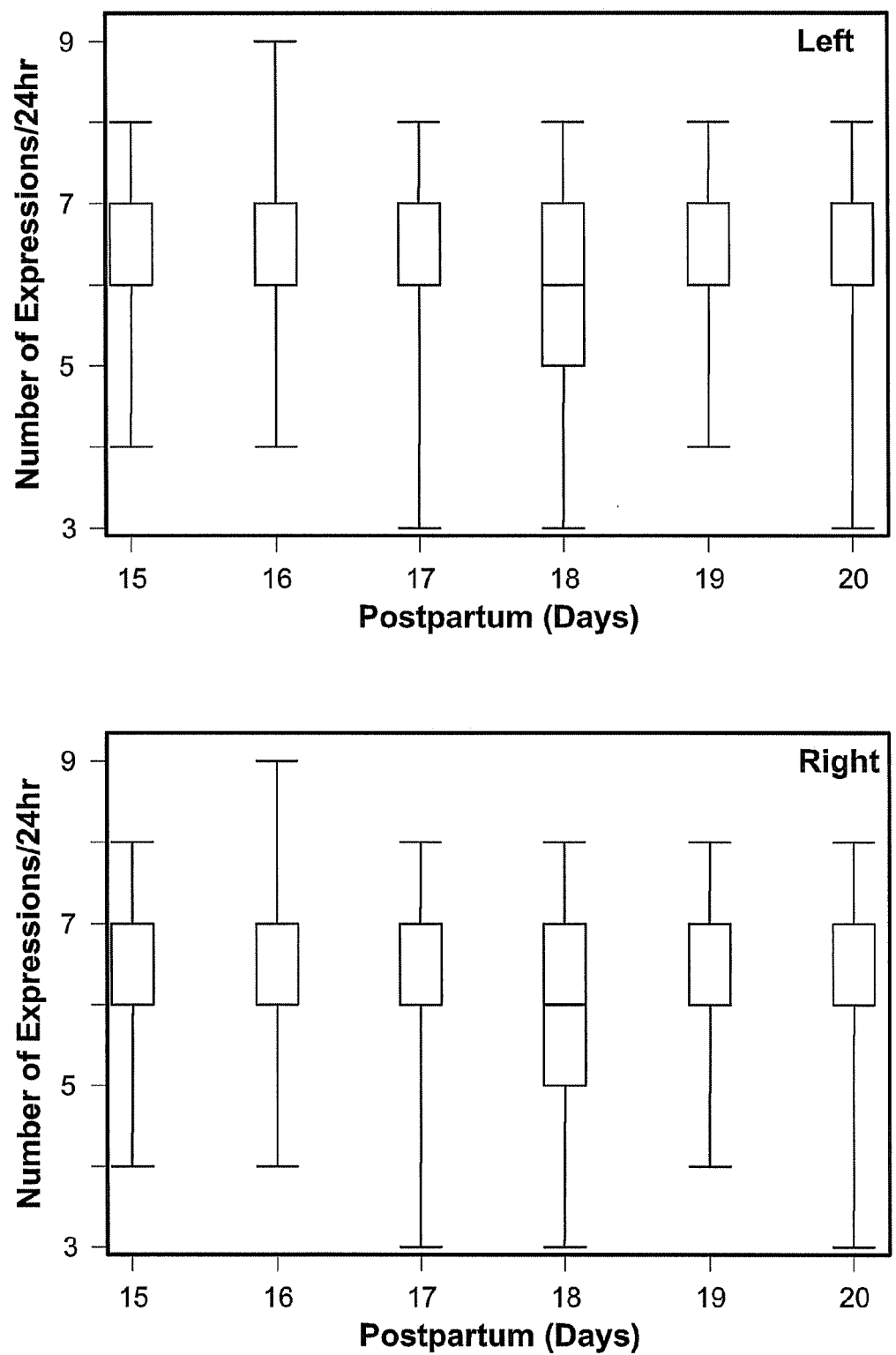
FIG. 5 shows frequency of expression for days 15 to 20 postpartum.
Figure 6:
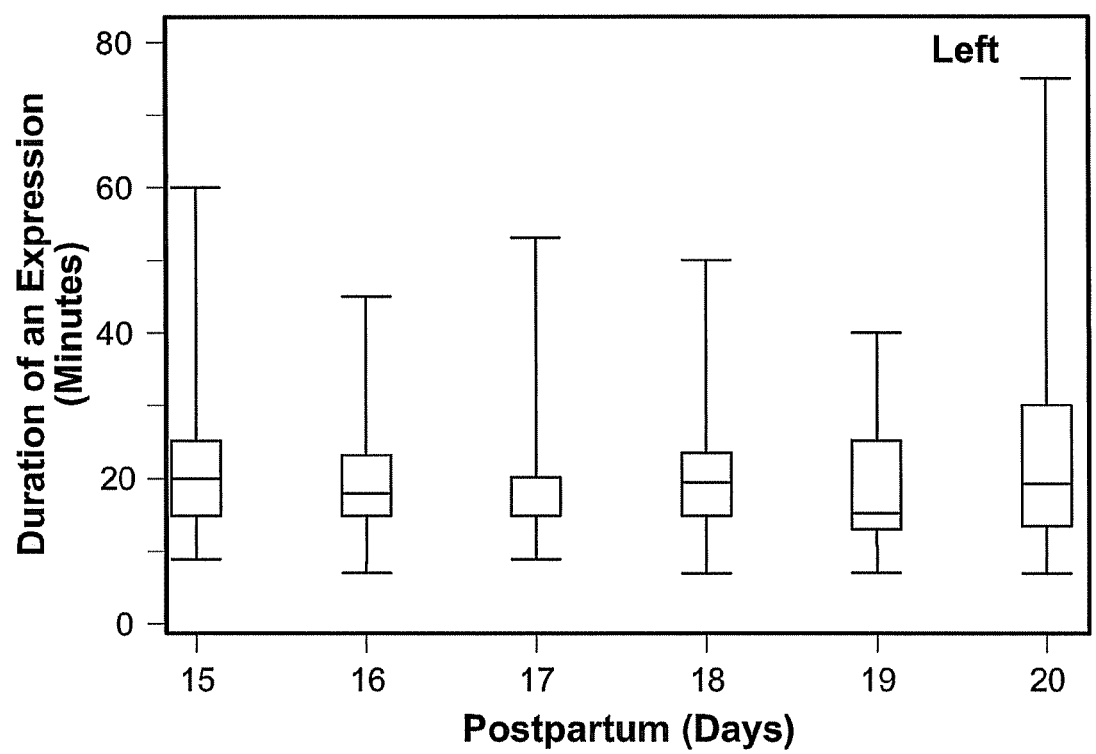
FIG. 6 shows duration of each expression per day.
Figure 6:
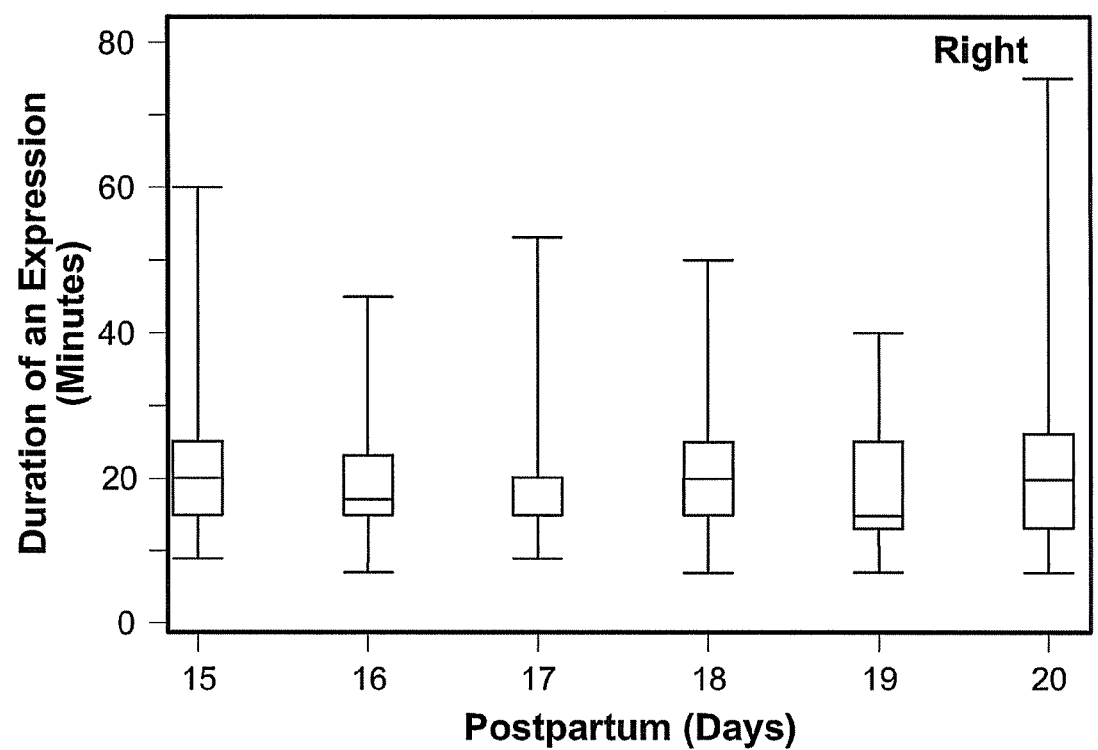
Figure 7:
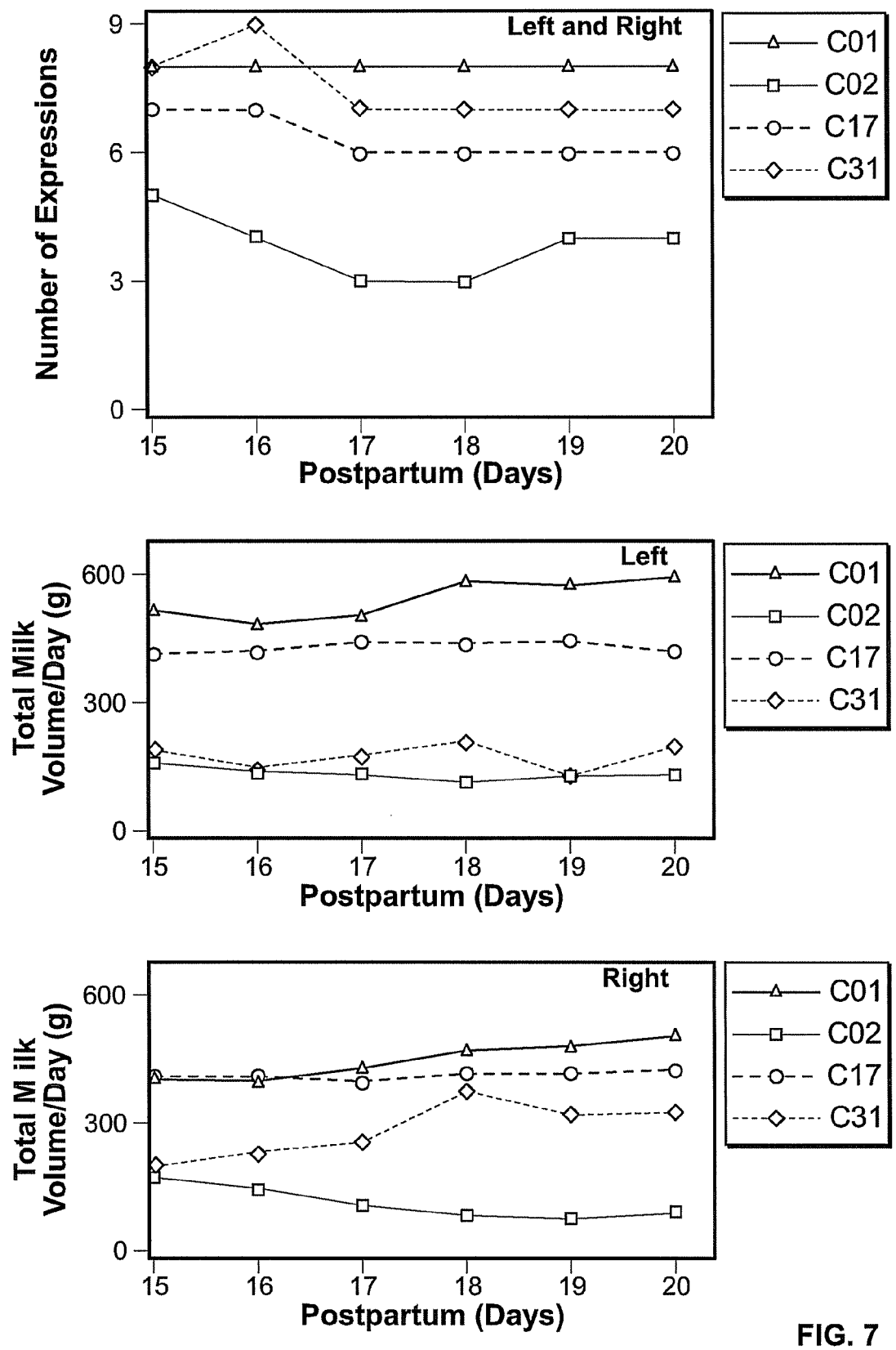
FIG. 7 shows frequency of expression and total milk volume per breast of individual mothers (C01, C02, C17 and C31) for days 15 to 20 postpartum.
Figure 8:
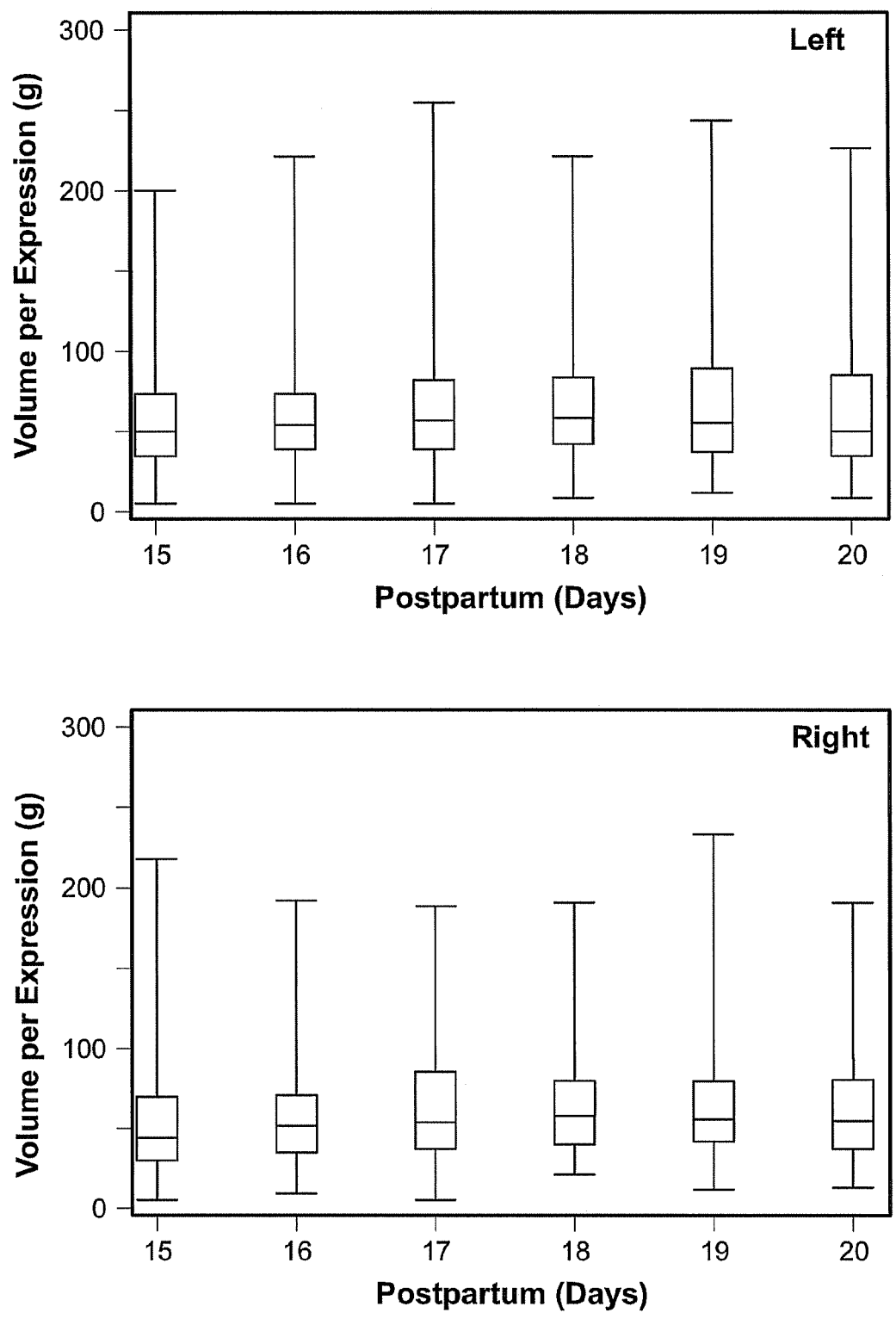
FIG. 8 shows volume of milk per expression for days 15 to 20 postpartum.

For each mother, the total volumes per day from the left and right breasts were very similar, but there were large variations between mothers (FIG. 4). The expression regimes of the left and right breasts of preterm mothers were similar. Overall, the mean volume per day per breast was not correlated to the mean frequency of expression per day per breast. The average volume of milk per expression for days 15 to 20 postpartum was 53, 37.3-81, 5.1-254.3 g and 54, 37-79, 3.2-257 g, for left and right breasts, respectively (FIG. 8).

The median, IQR and range of CV of the mothers for left and right breasts for milk volume were 26.0, 20.3-29.3, 11.5-70.0%, 23.4, 20.5-29.1, 12.6-52.7%; for interval since previous expression were 23.2, 20.1-25.9, 0-43%, 24.0, 18.1-26.3, 3.04-44.6% and for hour rate of milk yield were 21.0, 15.9-25.9, 12.3-62.3%, 20.2, 17.8-26.3, 10.3-48.6%, left and right breasts respectively.

Five mothers (C08, C17, C01, C02 and C31) are used to illustrate the pattern of variation of milk expression observed between mothers.

TABLE 1

Within mother variability

| Mother | Breast | Milk volume (g) | | | | Interval (hr) | | | | Hourly rate (g/h) | | | |
|---|---|---|---|---|---|---|---|---|---|---|---|---|---|
| | | Median | IQR | Range | CV(%) | Median | IQR | Range | CV(%) | Median | IQR | Range | CV(%) |
| C08 | Left | 131 | 107-164 | 79-180 | 24 | 5 | 4-7 | 3-7 | 30 | 28 | 26-29 | 24-33 | 9 |
| | Right | 152 | 122-190 | 91-198 | 23 | 5 | 4-7 | 3-7 | 30 | 32 | 30-34 | 27-37 | 9 |
| C17 | Left | 72 | 66-75 | 46-89 | 15 | 4 | 3-4 | 2-5 | 22 | 19 | 18-21 | 16-28 | 16 |
| | Right | 65 | 61-72 | 48-84 | 14 | 4 | 3-4 | 2-5 | 22 | 18 | 17-19 | 15-28 | 19 |
| C01 | Left | 64 | 53-79 | 38-103 | 27 | 2 | 2-3 | 2-4 | 24 | 24 | 22-29 | 18-44 | 24 |
| | Right | 55 | 43-70 | 8-112 | 37 | 2 | 2-3 | 2-4 | 24 | 20 | 17-28 | 3-41 | 43 |
| C02 | Left | 35 | 27-49 | 23-53 | 30 | 5 | 3-8 | 1-14 | 66 | 7 | 6-14 | 3-16 | 52 |
| | Right | 30 | 21-34 | 12-54 | 39 | 5 | 3-8 | 1-13 | 65 | 6 | 3-9 | 2-13 | 55 |
| C31 | Left | 15 | 10-31 | 5-72 | 77 | 3 | 2-3 | 2-5 | 26 | 5 | 4-8 | 2-23 | 73 |
| | Right | 40 | 21-53 | 6-100 | 60 | 3 | 2-3 | 2-5 | 26 | 15 | 8-18 | 2-22 | 47 |

CVs of all data between days 15 and 20 from each breast of each mother

Milk production at each expression from each breast was set forth as a proportion (%) of the 24-hour milk yield. The relationship between the proportion (%) of the 24-hour milk yield and interval since previous expression for each breast of the 23 mothers is presented in FIGS. 9 to 33. Forty of 46 breasts had significant correlations ($r=0.05$ to $0.85$ and $0.03$ to $0.84$, left and right breasts, respectively) between the proportion of milk yield and the interval since previous expression.

If milk was synthesized within the breast at a constant rate over the 24-hour period, then milk yield should relate to the interval since previous expression, according to the equation $mp=xt$ (where $mp=$milk yield (%), $x=$slope and $t=$interval since previous expression), such that the percentage of daily milk yield is 100% if the interval between the last expression was 24 hours (Daly et al., 1996). Each breast of each mother would have its own expected milk regression line ($mp=xt$), and the average x for the left breast was 4.18 and for the right breast was 4.19.

To aid in the interpretations of the results, 95% confidence intervals have been fitted to the actual regression lines and compared to the expected regression line. For the majority of breasts, the expected milk yield regression line was within the 95% confidence limits for the actual milk yields. In all breasts, except for those of one mother (C31), the actual milk yield regression line had either a similar slope and course to the expected regression line (see FIG. 10) or had a shallower slope and bisected the expected regression line (see FIG. 18). Of the 40 breasts with significant correlations between milk yield and interval between breast expressions, the slope of the actual regression line was similar to that of the expected line in eight breasts, that is, the actual slope was at least 80% of the expected slope. For the remaining breasts (except mother C31) with significant correlations, the actual slope was between 24-76% of the expected slope and the mean intercept between the actual regression line and the expected regression lines was 4.3±0.9 hours.

Figure 22:
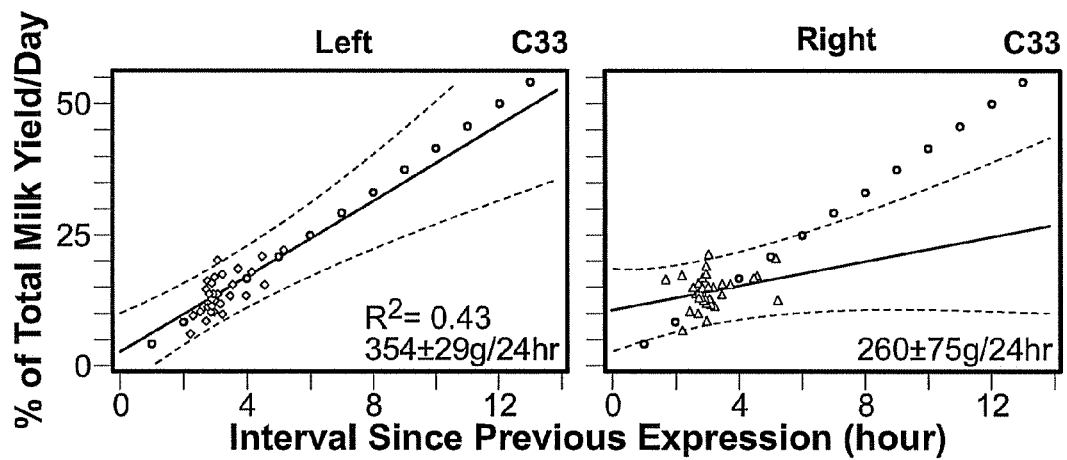
Figure 23:
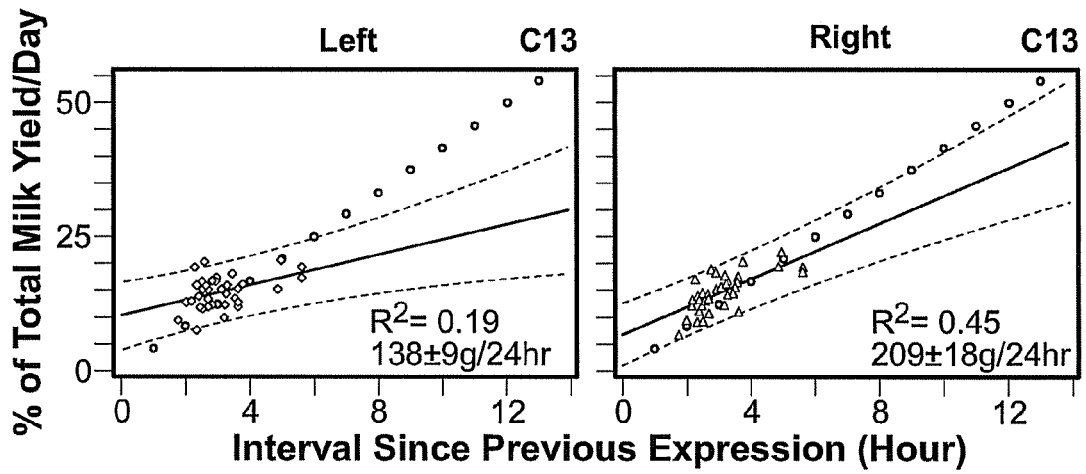
Figure 24:
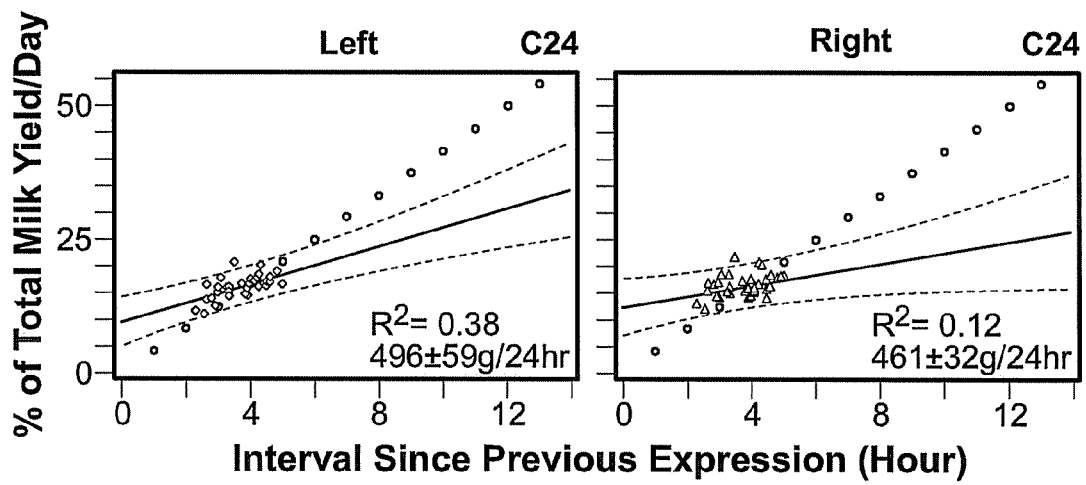
Figure 25:
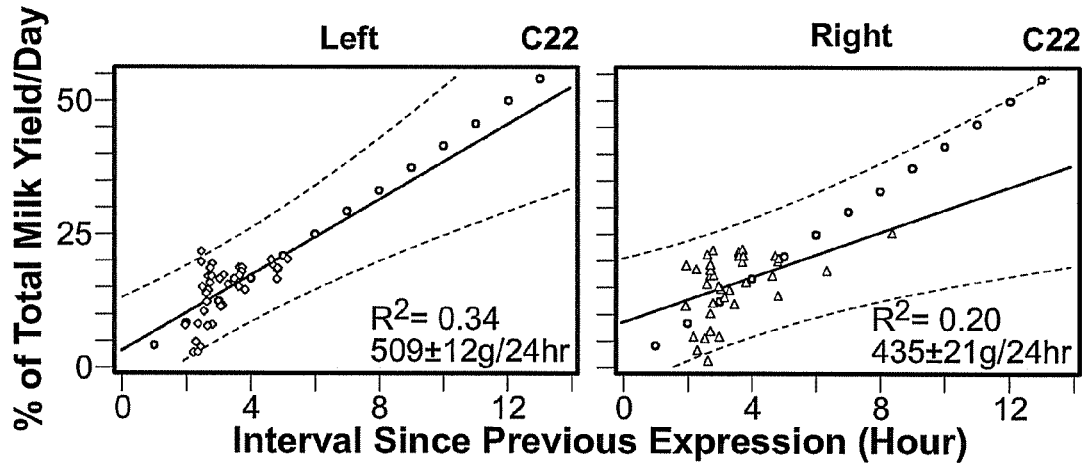
Figure 26:
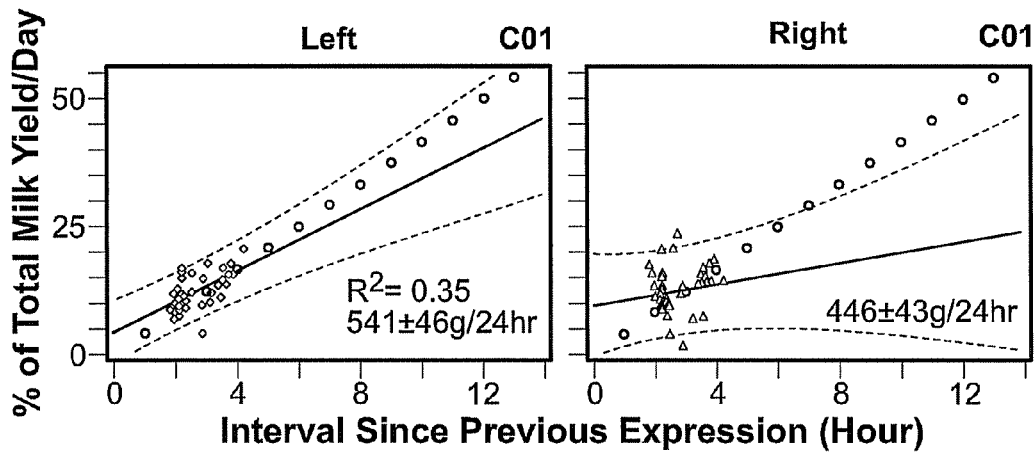
Figure 27:
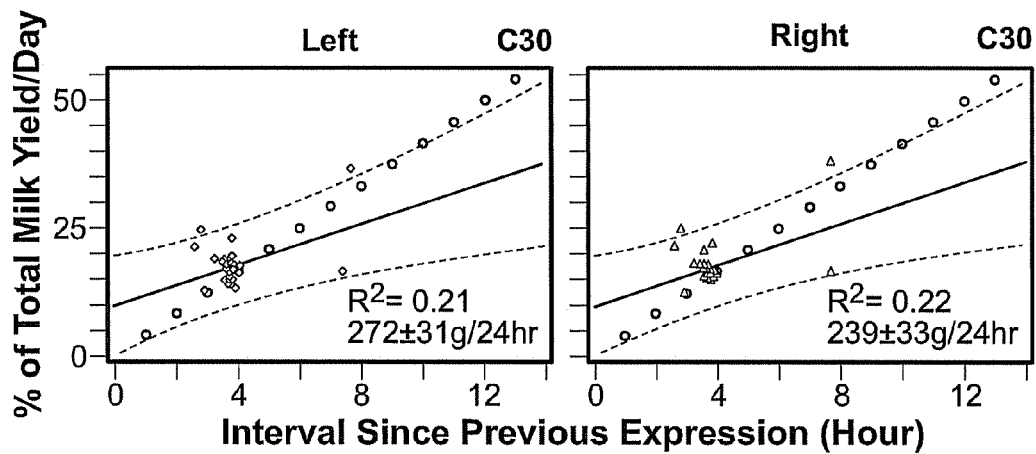

No standard statistical methods are available to compare the actual milk yield regression lines to the "expected" regression lines for the breasts that had significant correlations between milk yield and the interval since previous expressions. Yet a comparison of these regression lines has very important implications for expressing mothers. It is clear that the slopes of regression lines of the actual milk yields were greater than that of the expected milk yield in the left and right breast of only one mother (FIG. 22). In eight breasts the slopes of actual and expected milk yields were similar (within 80% of each other). Therefore, the longest interval chosen for the expression of these breasts did not compromise milk yield. These breasts could be expressed at the longer intervals without jeopardizing daily milk production. Of the eight breasts, four were the left and right breasts of four mothers. In the remaining 32 breasts, the actual milk yields intersected the expected milk yields regression lines such that, at shorter intervals between breast expressions, milk yield was higher than expected and at longer intervals it was lower than expected. This finding is consistent with both the findings for term mothers (Daly et al., 1996) and the autocrine control hypothesis (Wilde et al., 1998), that as milk accumulates in the breast the rate of milk synthesis is inhibited. Breasts with these regression patterns would be expected to respond to decreasing the longer intervals between breast expressions, if low milk supply was of concern.

Figure 9:
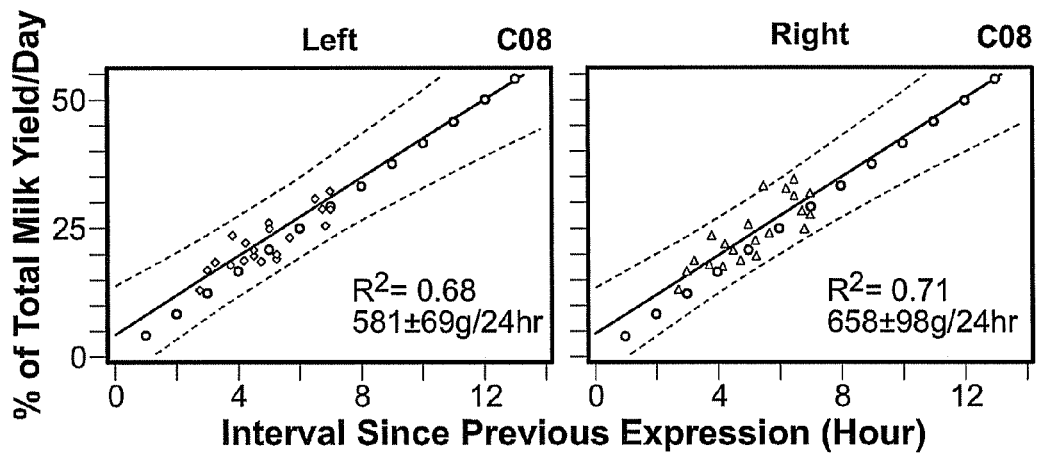
FIGS. 9 to 33 illustrate the regression graph for each illustrative mother.
Figure 10:
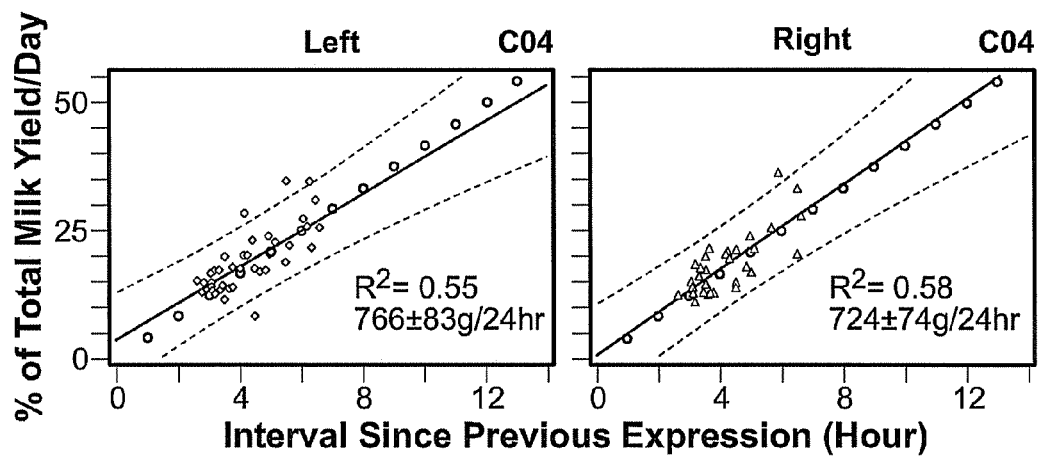
Figure 11:
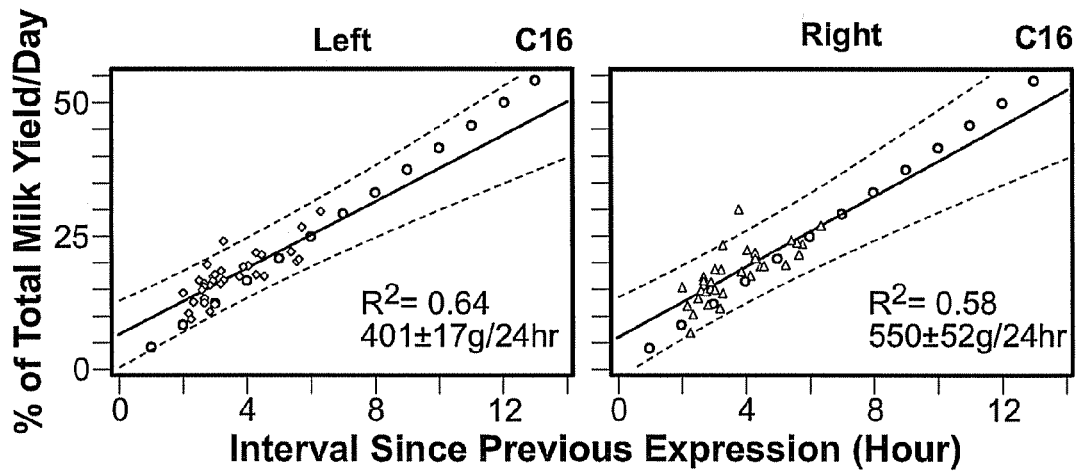
Figure 12:
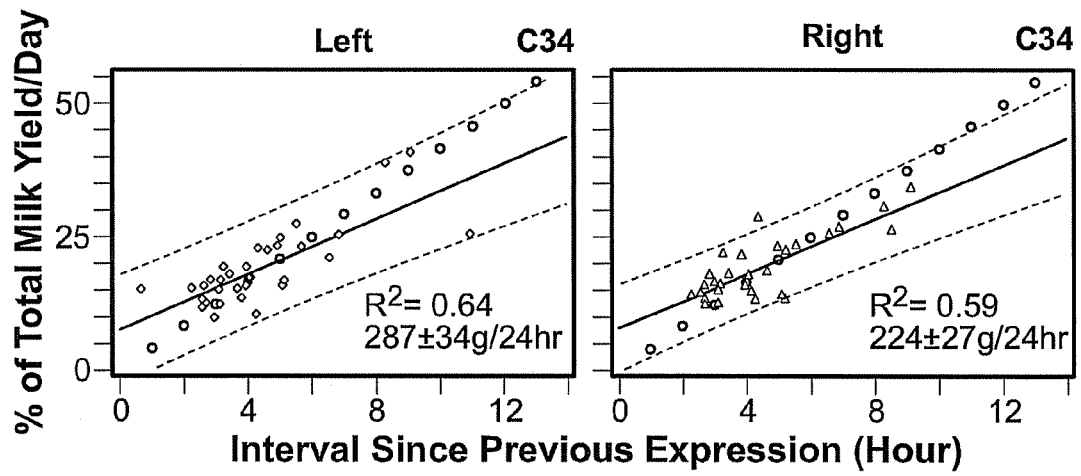
Figure 13:
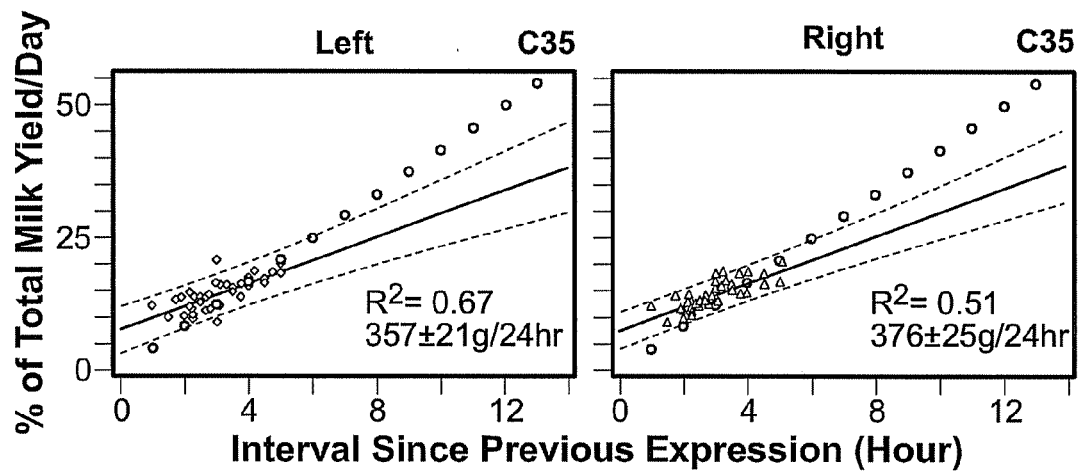
Figure 14:
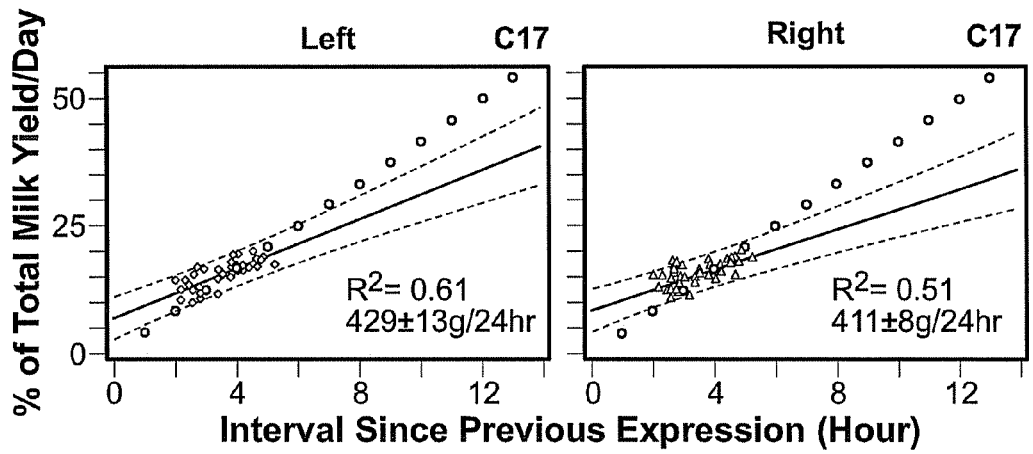
Figure 15:
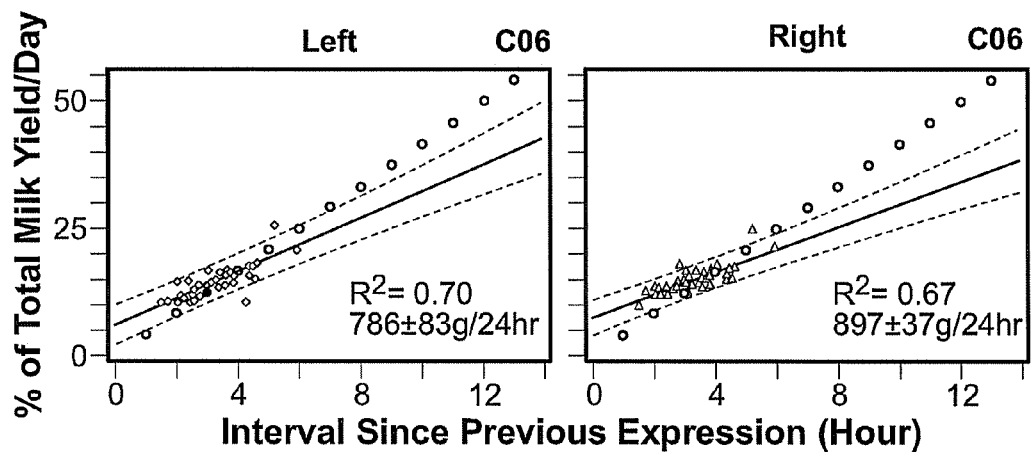
Figure 16:
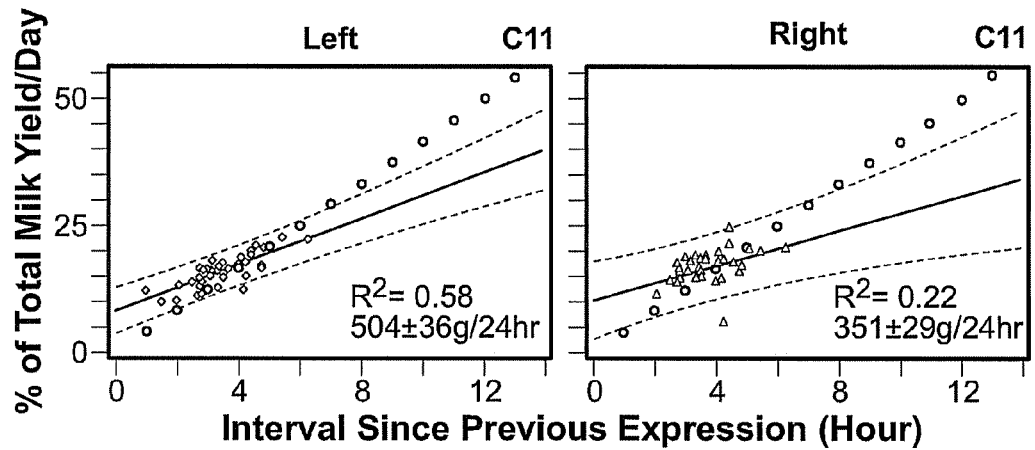
Figure 17:
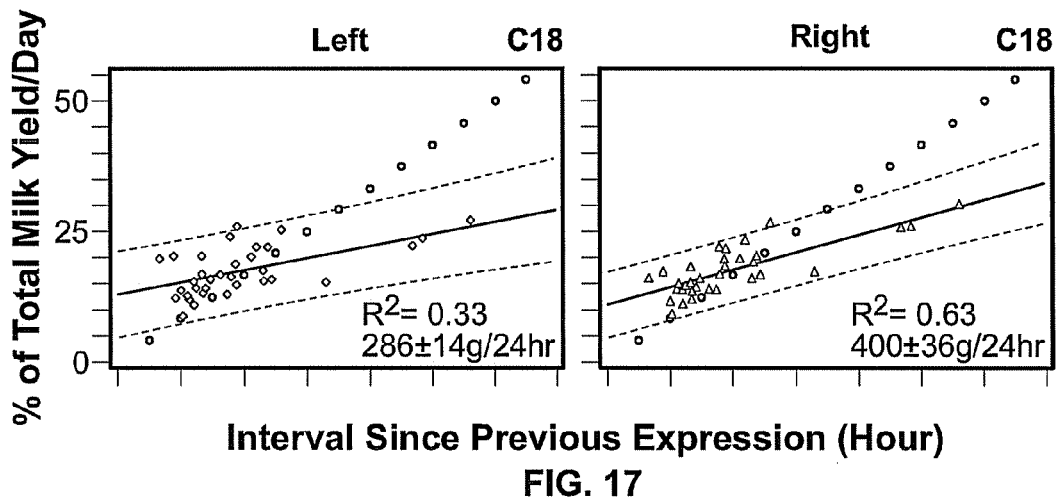
Figure 18:
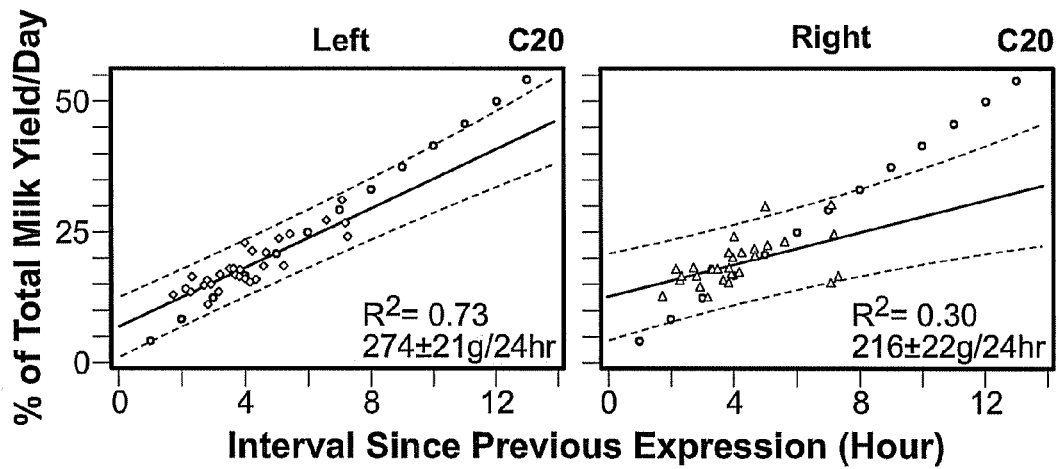

Specifically, the regression lines for the actual milk yields and the expected milk yields had similar slopes and intercepts for both breasts for three of 25 mothers (FIGS. 9-11). Furthermore, these mothers had high daily milk productions (>900 ml/24 hr). Their average frequency was 5.1±0.5 expressions per day per breast between days 15 and 20 postpartum. Since the relationship between proportion of 24 hour milk production and interval since previous expression for these mothers was highly correlated ($r=0.74$ to $0.84$), the milk yield from the breasts of these mothers would be unlikely to respond to changes in the expression regime.

This regression analysis therefore led to the conclusion that the interval of expression could extend from 4.8 to 7 hours without compromising the milk production. This would reduce the frequency of expression from 5 to 3.4 times per day, and save on average 48±14 minute at pump per day for each mother. Furthermore, since the median frequency for these mothers was 5, 50% of the time the mothers were expressing at intervals that were shorter than 4.7 hours with some intervals as short as 2-3 hours; therefore apart from decreasing the pumping time per day, the extended interval would enable the mothers much more flexibility in planning their daily activities.

The slopes of the regression lines for the actual milk yield and expected milk yield were different for 7 of 25 mothers (FIGS. 12-15, 20, 21 and 27), but similar responses were observed between the left and right breasts for each of these mothers. The daily milk production was >450 ml/24 hr (mean of 818±49 ml/24 hr). The average frequency of expression for these mothers was 6.2±0.5 and total duration at the pump was 112±14 minutes per day between days 15 and 20 postpartum. Extending the interval from 4 hours to 5 hours per expression predicts a similar daily milk production for these mothers, but the frequency of expression would be reduced from 6 to 4 times per day, and thereby save on average 34±8 minutes per day per breast. It is noted that here, the slope of the regression line of the actual milk yield shows that milk production was compromised with extended intervals between breastfeeds. In addition, there was a relatively large variation in the correlation between proportion of 24-hour milk production and interval since last expression ($r=0.45$ to $0.83$); therefore, it is likely that there would be a graded response between mothers in the improvement of the daily milk production associated with optimizing the interval between breast expressions.

Figure 19:
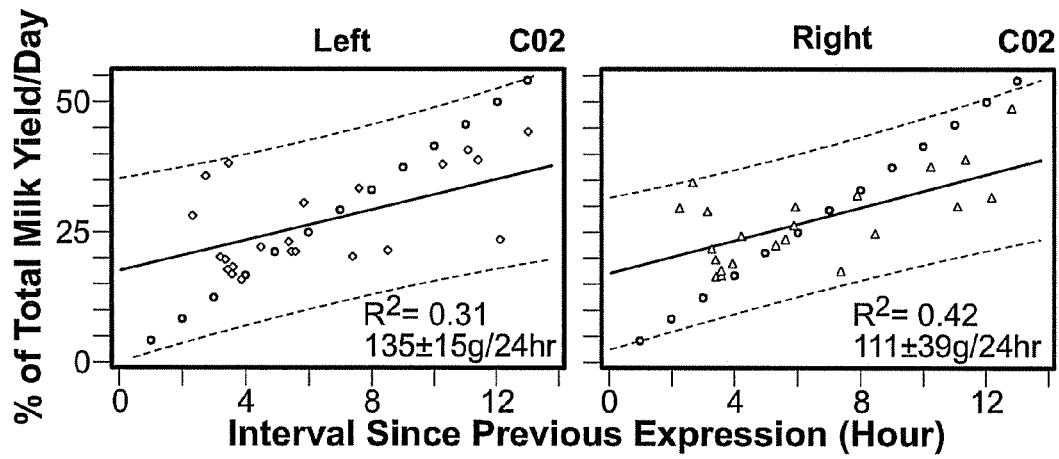
Figure 20:
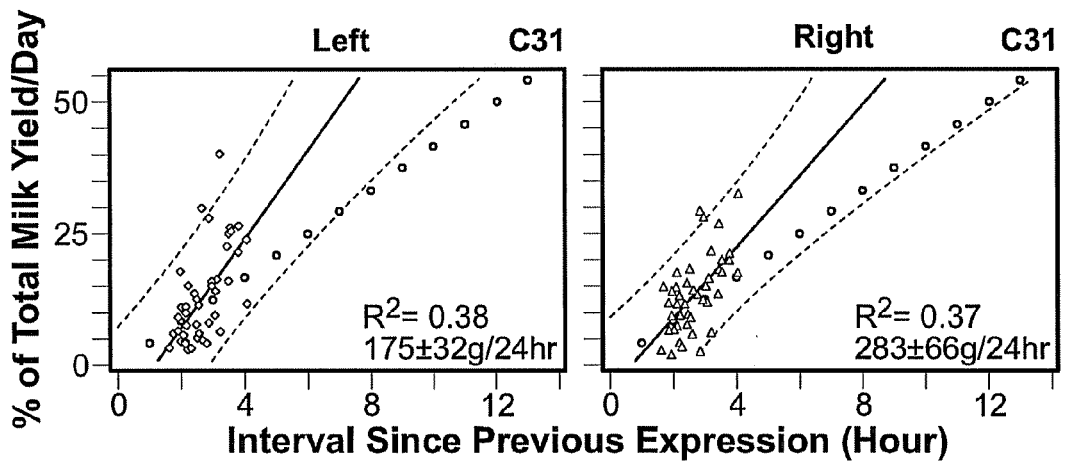
Figure 21:
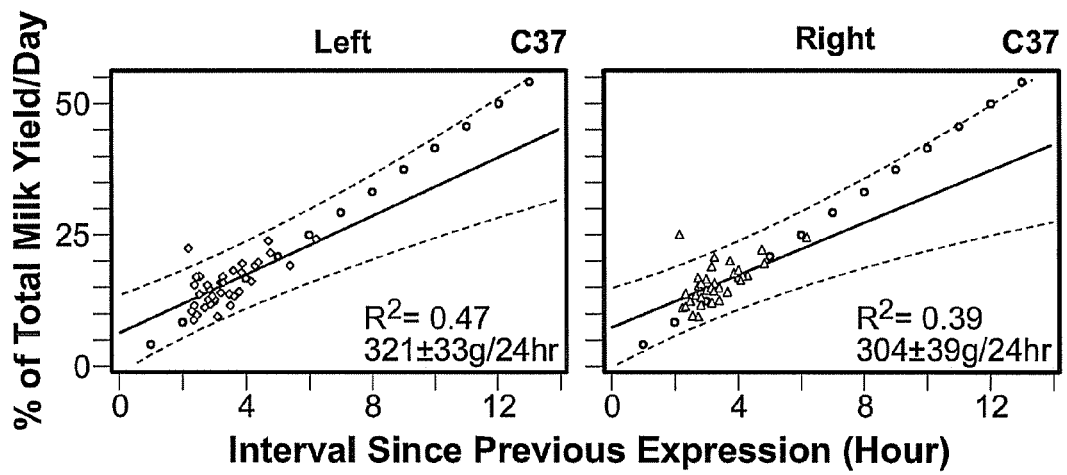
Figure 28:
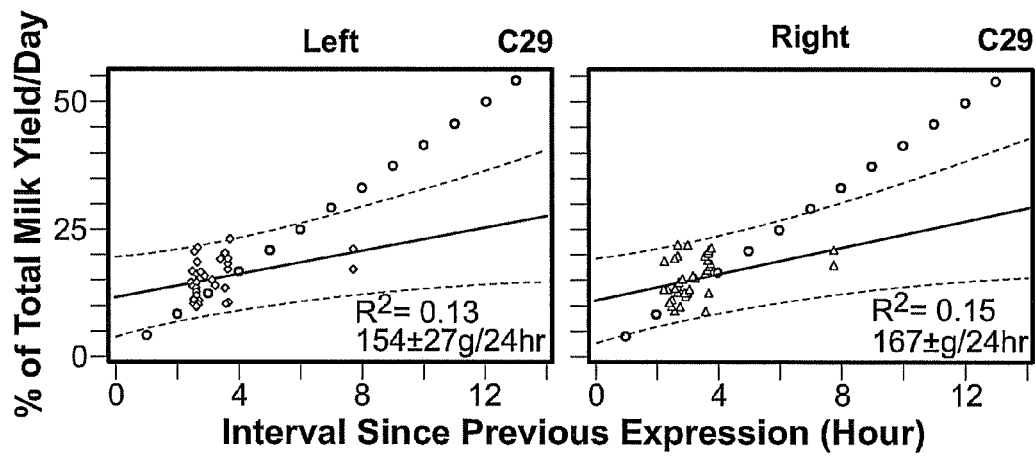
Figure 29:
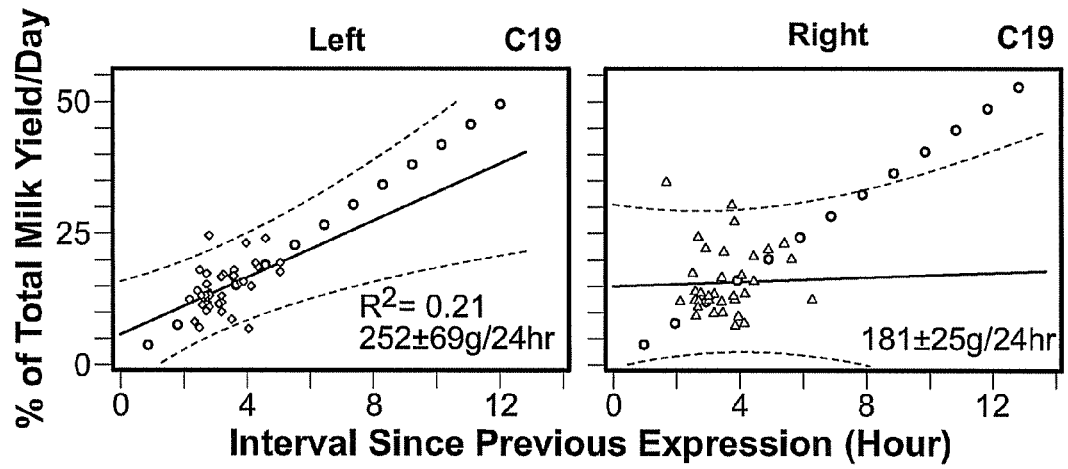
Figure 30:
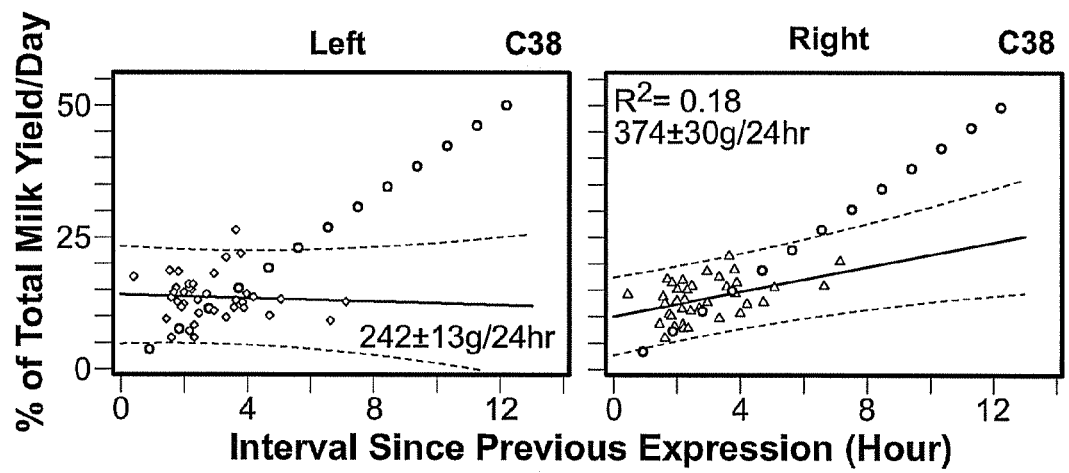
Figure 31:
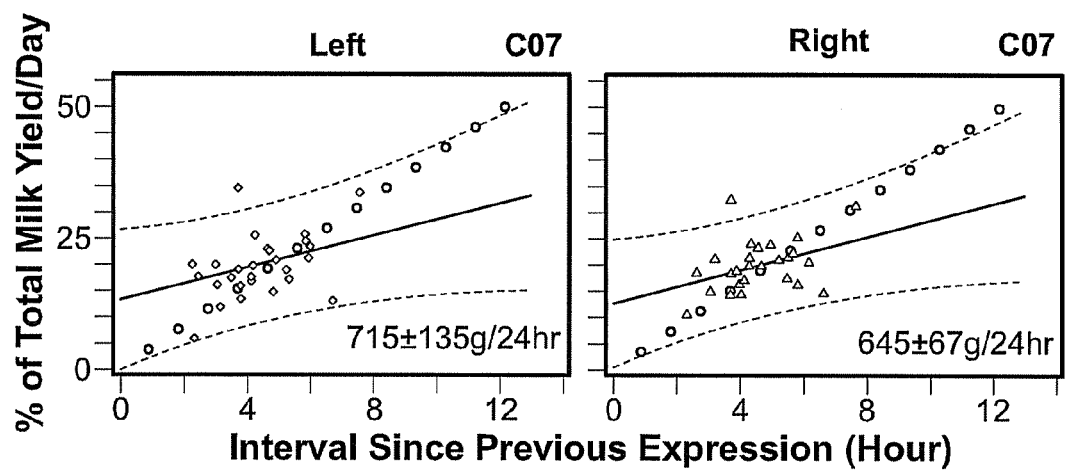
Figure 32:
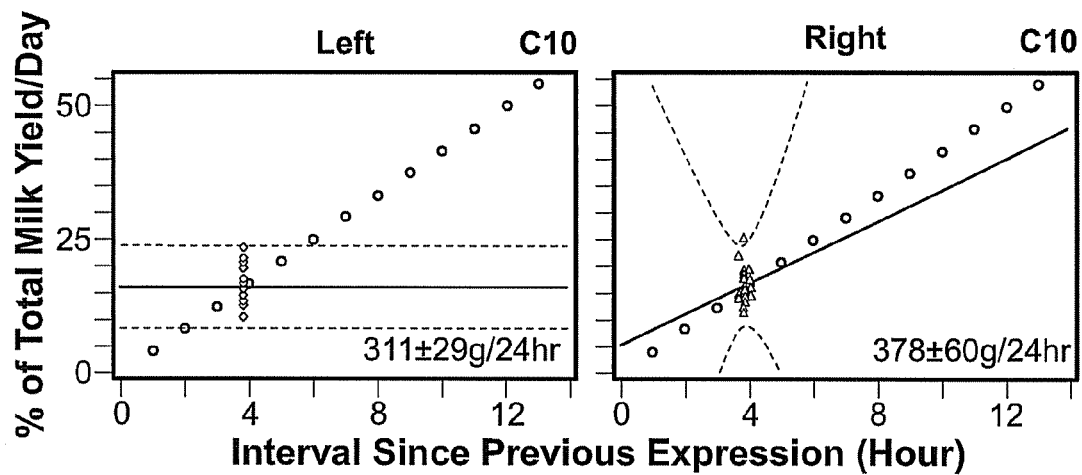
Figure 33:
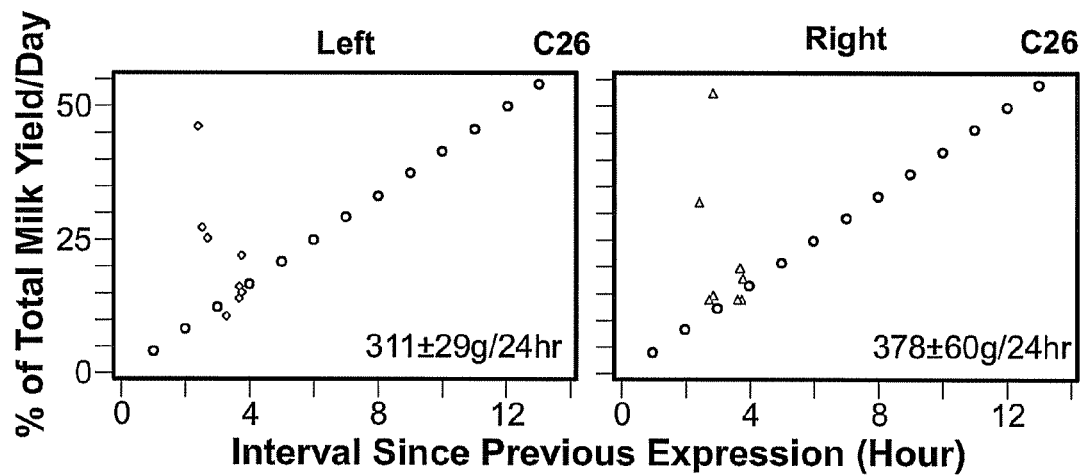

Two of 25 mothers had daily milk production less than 450 ml/24 h (246 ml/24 hr for mother in FIG. 19 and 321 ml/24 hr for mother in FIG. 28). The slopes of the regression lines for the actual milk yield and expected milk yield were different, but similar responses were observed between the left and right breasts for each mother. They expressed on average 5.3±0.6 times with per day between days 15 and 20 postpartum. The slope of the regression line predicts that there would be an improvement in both mothers' milk productions if the interval between breast expressions did not exceed 4 hours. According to the regression equation for the actual milk yield for both breasts in FIG. 19, 23% of 24-hour milk production should be achieved at 4 hour intervals. On this basis, it was predicted that 4 hour intervals would result in an increase of 38% in the 24-hour milk yield per breast, and therefore an increase of 72% in total daily milk production for both breasts. That is, an extra of 177 ml/24 hr would be obtained with an expression interval of 4 hours and her daily milk production would increase to 423 ml/24 hr. For the mother in FIG. 28, 4 hour intervals would result in an increase of 16% in the 24-hour milk yield per breast and therefore increase her total daily milk production by 32%, that is, increasing her daily milk production to 437 ml/24 hr. However, since the correlation between proportion of 24-hour milk production and interval since previous expression for each mother was not very strong ($r=0.36$ to $0.64$), the predicted improvement in milk production by reducing the longer intervals between breast expressions would be a maximum expected response.

The slopes of the regression lines for the actual milk yields and expected milk yields between the left and right were different for eight of 25 mothers (FIGS. 12-18 and 22-26). These eight mothers had average daily milk production of greater than 450 ml/24 hr (mean 770±52 ml/24 hr). Three of these mothers (FIGS. 12-18) had only one breast that had a relatively high correlation ($r=0.76-0.85$) between the proportional of 24-hour milk production and interval since last expression and the other breast had a low correlation ($r=0.47-0.57$). Extending the interval of expression up to 5 hours for these mothers would not be considered to cause a significant decrease in milk production. One breast of the remaining five mothers had a low correlation ($r=0.58-0.66$) and the other breast had either lower or no correlation ($r=0.00-0.45$) between the proportion of 24-hour milk production and interval since previous expression. Therefore, extending the interval of expression up to 4 hours for these mothers would not be considered to cause a significant decrease in milk production, as this is still within the range of intervals chosen by these mothers. The high milk production of these mothers provides additional confidence in the likely success of the above method.

In contrast to the above eight mothers, two mothers (FIGS. 23 and 29) showed differences in the slopes of the regression lines for the actual milk yields and expected milk yields of the left and right breasts to the above eight mothers. But in contrast these two mothers had low milk productions, 340 and 433 ml/24 hr, respectively. However, the average interval between breast expressions for these mothers was 3.0±1.9 hr and 3.5±1.1 hr, respectively. Furthermore, the relationship between the proportion of 24-hour milk production and interval since previous expression accounted for 19% and 45%, and 21% and 0% of the variation in milk yield for their left and right breasts respectively. Therefore, decreasing the interval between breast expressions would be predicted to be unlikely to increase milk production for these mothers.

While certain features and embodiments of the present application have been described in detail herein, it is to be understood that the application encompasses all modifications and enhancements within the scope and spirit of the following claims.

What is claimed is:

1. A method for administering a milk expression protocol for a nursing mother using a breastpump, comprising the steps of:
   measuring a volume of milk expressed from the mother using the breastpump, the milk being produced in at least three pumping sessions, where the breastpump is used to express milk from the mother and where a first pumping session is the first milk expression for a day, a second pumping session next occurs after the first pumping session, and a following pumping session is after the second pumping session on the same day,
   defining the volume of milk expressed in the following pumping session to be an average yield of milk production per pumping session,
   performing a regression analysis to calculate an amount that an interval of expression used by the nursing mother is extendable without compromising a daily total volume of milk produced, wherein the daily total volume of milk produced is calculated based on the defined average yield of milk production per pumping session, and
   providing an expression protocol for the mother based upon the regression analysis comprising the amount that the interval of expression can be extended by the mother.

2. The method of claim 1, wherein the defined average yield of milk production per pumping session taken from a single pumping session is defined to be an estimate of average hourly milk production for a 24-hour period.

3. The method of claim 2 wherein the number of pumping sessions is six, each of which is separated in time by about one hour.

4. The method of claim 2 wherein the average yield of milk production is multiplied by twenty-four to obtain assessed daily milk production capacity.

5. The method of claim 1 wherein the following pumping session is a third pumping session.

6. The method of claim 5 wherein the number of pumping sessions is six.

7. The method of claim 5 wherein the number of pumping sessions is seven.

8. The method of claim 1 wherein the following pumping session is selected from one of a third or subsequent pumping session.

9. The method of claim 1 wherein the pumping sessions are separated from each other by about one hour.

10. The method of determining milk production capacity of a nursing mother of claim 1 wherein the following pumping session is the pumping session that occurs after the second pumping session.

11. A method comprising:
using a breastpump to express milk from a mother at least three intervals during a day;
determining a quantity of milk expressed at a third or subsequent interval of the at least three intervals;
defining the quantity of milk expressed at the third or subsequent interval as an average quantity of milk expressed for any pumping session on the same day;
performing a regression analysis to calculate an amount that the interval of expression is extendable without compromising a daily total volume of milk produced, wherein the daily total volume of milk produced is calculated based on the defined average yield of milk production per pumping session, and
providing an expression protocol for the mother comprising the calculated amounts that the interval of expression can be extended without compromising milk production, the calculated amount predicted being based upon the defined average quantity of milk.

12. The method of claim 11 wherein the intervals are separated by about five to about seven hours.

13. A method of administering a milk expression protocol considering milk production capacity of a nursing mother using a breastpump, the method comprising the steps of:
measuring a volume of milk expressed from the mother using the breastpump being produced in at least three pumping sessions during a day, wherein the breastpump is used to express milk from the mother,
detecting a period of time wherein there is an initial high volume milk output in one of the at least three pumping sessions relative to at least two of the at least three pumping sessions, the at least two pumping sessions following thereafter on the same day,
defining the pumping session with the initial high volume output as a first pumping session and defining a next subsequent breastpumping session as a second pumping session,
measuring a volume of milk produced in a breastpumping session of the at least three pumping sessions, the breastpumping session following the second pumping session,
defining the determined volume of milk produced in the breastpumping session following the second pumping session as an average yield and
performing a regression analysis to calculate an amount that an interval of expression used by the nursing mother is extendable without compromising a daily total volume of milk produced, wherein the daily total volume of milk produced is calculated based on the defined average yield of milk production per pumping session, and
providing an expression protocol to the mother wherein the defined average yield and the regression analysis are used to optimize milk production while minimizing the frequency of milk expression by the mother.

14. The method of determining milk production capacity of a nursing mother of claim 13, wherein the average yield represents an estimate of average hourly milk production for a 24-hour period.

15. The method of determining milk production capacity of a nursing mother of claim 13 wherein the following pumping session is next following the second pumping session.

16. The method of determining milk production capacity of a nursing mother of claim 13 wherein the following pumping session is selected from one of a third pumping session or pumping session subsequent to the third pumping session.

* * * * *